US012802826B2

(12) United States Patent
Agurto Rios et al.

(10) Patent No.: US 12,802,826 B2
(45) Date of Patent: Nov. 17, 2026

(54) MONITORING AND FACILITATING ACTIONS FOR A PATIENT TO ATTAIN DESIRED HEALTH

(71) Applicant: International Business Machines Corporation, Armonk, NY (US)

(72) Inventors: Carla Paola Agurto Rios, Ossining, NY (US); Erhan Bilal, Westport, CT (US); Pritish Ranjan Parida, Cortlandt Manor, NY (US); Jenna Reinen, Rye Brook, NY (US); Tigran Tigran Tchrakian, Castleknock (IE); Jeffrey L. Rogers, Briarcliff Manor, NY (US)

(73) Assignee: International Business Machines Corporation, Armonk, NY (US)

( * ) Notice: Subject to any disclaimer, the term of this patent is extended or adjusted under 35 U.S.C. 154(b) by 178 days.

(21) Appl. No.: 18/635,276

(22) Filed: Apr. 15, 2024

(65) Prior Publication Data

US 2025/0322966 A1 Oct. 16, 2025

(51) Int. Cl.
*G16H 50/70* (2018.01)

(52) U.S. Cl.
CPC .................................. *G16H 50/70* (2018.01)

(58) Field of Classification Search
CPC ...................................................... G16H 50/70
See application file for complete search history.

(56) References Cited

U.S. PATENT DOCUMENTS

2006/0026036 A1 2/2006 Mahmood
2014/0244292 A1 8/2014 Rosenberg et al.
2014/0350954 A1 11/2014 Ellis et al.
2015/0006193 A1 1/2015 Dadlani Mahtani et al.
2018/0301209 A1 10/2018 Kim et al.
2019/0108769 A1 4/2019 Contant et al.
2021/0104173 A1 4/2021 Pauley et al.
2021/0118578 A1 4/2021 Bettencourt-Silva et al.

FOREIGN PATENT DOCUMENTS

WO 03104939 A2 12/2003
WO WO-2004047624 A2 * 6/2004 ........... A61B 5/0002
WO WO-2015023674 A1 * 2/2015 ............. G16H 50/30

OTHER PUBLICATIONS

Ranjan, C., Paynabar, K., Helm, J.E. and Pan, J. (2017), The Impact of Estimation: A New Method for Clustering and Trajectory Estimation in Patient Flow Modeling. Prod Oper Manag, 26: 1893-1914. (Year: 2017).*

Allam A, Feuerriegel S, Rebhan M, Krauthammer M Analyzing Patient Trajectories With Artificial Intelligence J Med Internet Res 2021;23(12):e29812 (Year: 2021).*

Koren, et al., Matrix Factorization Techniques for Recommender Systems, Retrieved from: https://datajobs.com/data-science-repo/Recommender-Systems-[Netflix].pdf, Aug. 2009, pp. 42-49.

* cited by examiner

*Primary Examiner* — Eliza A Lam
(74) *Attorney, Agent, or Firm* — Harrity & Harrity, LLP

(57) ABSTRACT

According to a present invention embodiment, a machine learning model clusters data from a population of patients to determine a plurality of health states with each cluster corresponding to a health state. Transition costs are determined for transitioning between the health states. A path through the health states to the desired state of health for the patient is identified based on patient information. A set of actions for the patient is determined to traverse the health states of the path to attain the desired state of health.

24 Claims, 6 Drawing Sheets

MONITORING AND FACILITATING ACTIONS FOR A PATIENT TO ATTAIN DESIRED HEALTH

PARTIES TO A JOINT RESEARCH AGREEMENT

The present subject matter was developed and the claimed invention was made by or on behalf of Boston Scientific Neuromodulation Corporation and International Business Machines Corporation, parties to a joint research agreement that was in effect on or before the effective filing date of the claimed invention, and the claimed invention was made as a result of activities undertaken within the scope of the joint research agreement.

BACKGROUND

1. Technical Field

Present invention embodiments relate to health monitoring systems, and more specifically, to monitoring a patient and facilitating a course of action to enable the patient to attain an improved state of health.

2. Discussion of the Related Art

Most health treatments are focused on average symptoms of a patient population. Accordingly, some patients fail to reach a healthiest state (constrained by their condition) after treatment (given that treatments are not adapted to them). Although medical doctors use their experience and/or knowledge in helping improve health of a patient, it is difficult for the medical doctors to include similar behavioral aspects of an overall patient population in order to establish a more personalized treatment.

Health treatments work well to improve most common symptoms. However, the health treatments are constrained to solving a few aspects (failing to reach an optimal health state for each patient), and are not optimized to reduce recovery time. Although personalized treatments have been explored with some success, these treatments merely consider two health states (e.g., from sick to healthy) and fail to account for a trajectory of intermediate health states that enable improvement in health.

SUMMARY

According to one embodiment of the present invention, a system for facilitating actions for a patient to attain a desired state of health comprises one or more memories and at least one processor coupled to the one or memories. The system clusters, via a machine learning model, data from a population of patients to determine a plurality of health states with each cluster corresponding to a health state. Transition costs are determined for transitioning between the health states. A path through the health states to the desired state of health for the patient is identified based on patient information. A set of actions for the patient is determined to traverse the health states of the path to attain the desired state of health. Embodiments of the present invention further include a method and computer program product for facilitating actions for a patient to attain a desired state of health in substantially the same manner described above.

BRIEF DESCRIPTION OF THE DRAWINGS

Generally, like reference numerals in the various figures are utilized to designate like components.

DETAILED DESCRIPTION

Figure 1:
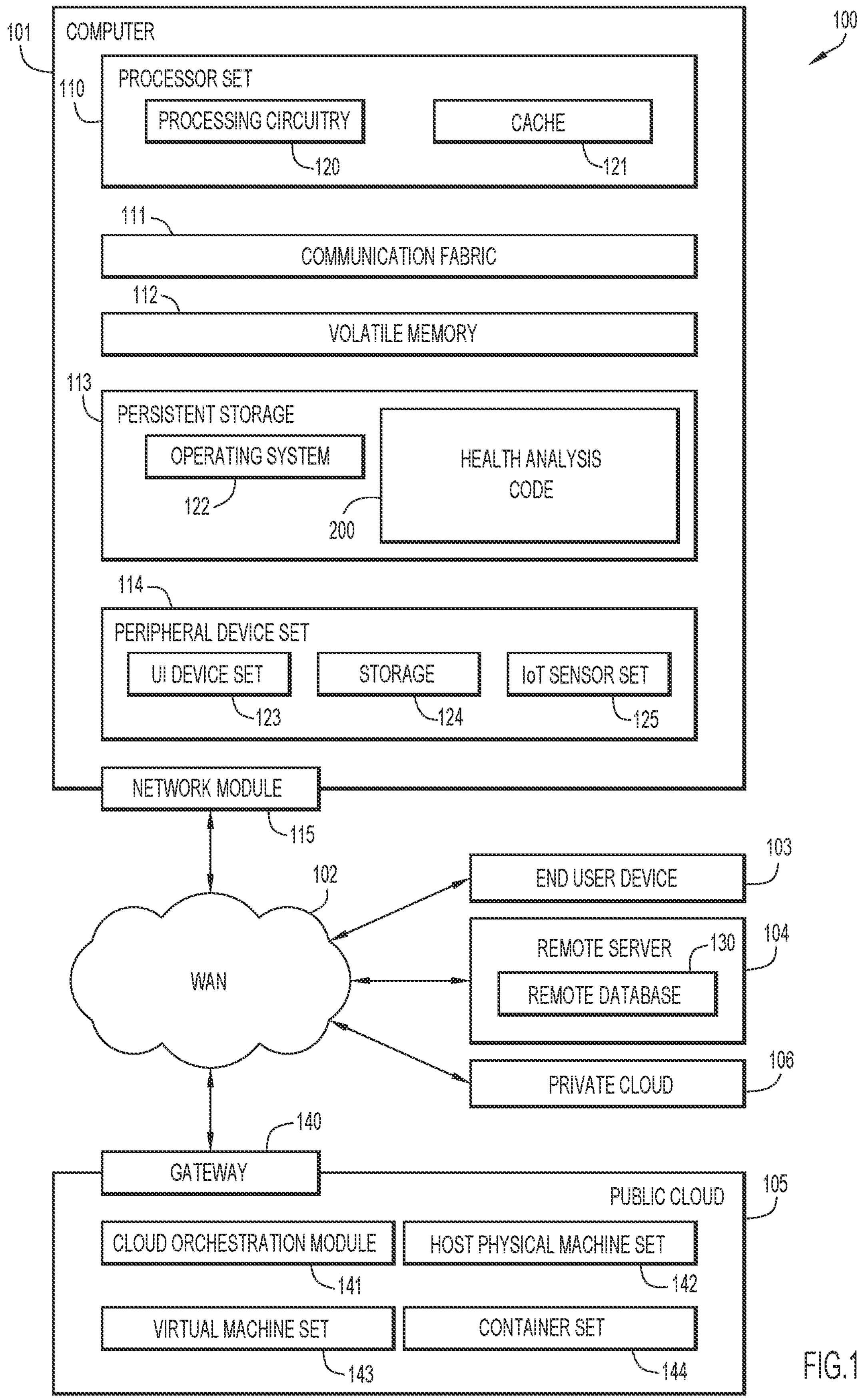
FIG. 1 is a diagrammatic illustration of an example computing environment according to an embodiment of the present invention.

Health improvement for a patient may include performing a set of actions across configurations of symptoms to return the patient to a healthy state. Patients do not necessarily follow the same path (or set of actions) to improve their health. However, the patients can share certain conditions and/or behaviors with a portion of a patient population that can help identify similarities (e.g., transition costs, etc.) in health transitions. Accordingly, an embodiment of the present invention identifies a sequence of health states that a patient (e.g., any user, individual, subject, or other entity with or without medical service provider care or supervision, etc.) should traverse in order to achieve their best possible health state.

A best path (or set of actions) for a patient through their healing journey is not necessarily the shortest path. A high initial transition cost of transitioning to an initial improved health state can be demoralizing and, thus, hamper progress. In addition, a best health state can vary between patients or be completely inaccessible for some patients. Accordingly, an embodiment of the present invention considers population-based measures of health transition costs, but also individualized measures (e.g., patient goals, patient psychology, etc.) in order to recommend a best pathway (or set of actions) to attain better health.

An embodiment of the present invention improves a patient health outcome. Patient health data is gathered from one or more patients, and health states and their relative ranking are identified. The relative ranking of the health states may be achieved based on patient preference, or patient resilience or tolerance obtained from standardized assessment instruments (e.g., fear avoidance and beliefs questionnaire, etc.). Transition costs between the health states are identified. The transition costs may be identified based on patient preference, or a frequency of transitions in a population cohort. The path to the best health state of a given patient is identified. The path between a patient current health state and the best health state may be a shortest path independent of transition costs, a path with the lowest total transition cost, a path with the lowest initial transition cost, or a path with the lowest individual transition costs. The path between a current health state and a best health state may be selected based on patient preference, or patient resilience. For example, a shortest path independent of transition costs may be selected when the resilience of the patient is high, a path with the lowest total transition cost may be selected when the resilience of the patient is medium-high, a path with the lowest initial transition cost may be selected when the resilience of the patient is medium-low, and a path with the lowest individual transition costs may be selected when the resilience of the patient is low. The level of resistance may be based on a numeric value derived from standardized assessment instruments for resilience and applied to a range for resilience levels.

An embodiment of the present invention identifies different health states of a patient population using clustering on available and relevant data (e.g., lab work, questionnaires (e.g. to ascertain mood, depression, quality of life, resilience, etc.), electronic medical records (EMR), sensors, etc.). A state transition matrix is generated for each patient using longitudinal patient data. The state transition matrix indicates a transition cost for transitioning between health states. A collaborative filtering technique is employed to ascertain missing data in the state transition matrix. Patient goals and resiliency are assessed based on standard questionnaires (e.g., pain catastrophizing scale, etc.). A personalized health state path (or set of actions for traversing) through the health states is determined based on the state transition matrix and assessment. The path may be determined based on a shortest path independent of transition costs, a path with the lowest total transition cost, a path with the lowest initial transition cost, or a path with the lowest individual transition costs.

According to an aspect of the invention, there is provided a method of facilitating actions for a patient to attain a desired state of health. The method clusters, via a machine learning model of at least one processor, data from a population of patients to determine a plurality of health states with each cluster corresponding to a health state. The method further determines, via the at least one processor, transition costs for transitioning between the health states, and identifies, via the at least one processor, a path through the health states to the desired state of health for the patient based on patient information. The method determines, via the at least one processor, a set of actions for the patient to traverse the health states of the path to attain the desired state of health. The machine learning model evolves based on new data to continually provide updated or new health states. This provides a dynamic arrangement that may continually change and adapt to patients. In addition, various health states may be introduced to provide more personalized sets of actions for a patient. This also reduces training or processing time as the machine learning model may be incrementally trained on new smaller training sets.

In embodiments, the health states are ranked, via the at least one processor, based on one of patient preference and resilience of the patient determined from results of standardized assessment instruments. This enables the embodiments to identify optimal paths and sets of actions that incrementally improve health according to patient tolerances. Further, the ranking reduces processing since the ranking provides a limited number of paths for improving health.

In embodiments, the transition costs between the health states are determined based on a count of transitions between the health states within the patient information and/or the data from the population. This enables the embodiments to weight paths according to population tolerances and provide a personalized set of actions suitable for the patient.

In embodiments, at least one transition between the health states is absent from the patient information, and a transition cost for the at least one transition between the health states is determined based on collaborative filtering of the data from the population. This enables the embodiments to accurately predict the transition costs for identification of paths and actions with improved results.

In embodiments, identifying the path through the health states comprises selecting and performing a path identification technique of one of: identifying a shortest path independent of the transition costs; identifying a path with a lowest total transition cost; identifying a path with a lowest initial transition cost; and identifying a path with lowest individual transition costs. This enables the embodiments to identify various different paths and actions to personalize the actions for a patient for enhanced results. Further, selection of different techniques reduces processing as a longest running technique is implemented less frequently.

In embodiments, the path identification technique is selected based on a preference of the patient. This enables the embodiments to customize the identification of the path and set of actions for a patient. Further, selection of different techniques reduces processing as a longest running technique is implemented less frequently.

In embodiments, the path identification technique is selected based on a resilience of the patient determined from results of standardized assessment instruments. This enables the embodiments to customize the identification of the path and set of actions to tolerances of the patient for improved results. Further, selection of different techniques reduces processing as a longest running technique is implemented less frequently.

In embodiments, a health device is controlled, via the at least one processor, to facilitate performance of the set of actions. This enables the embodiments to facilitate the identified set of actions for a path for expediting the process. Further, automated control of the health device reduces configuration time to expedite processing.

According to an aspect of the invention, a system facilitates actions for a patient to attain a desired state of health and comprises one or more memories and at least one processor coupled to the one or memories. The system clusters, via a machine learning model, data from a population of patients to determine a plurality of health states with each cluster corresponding to a health state. Transition costs are determined for transitioning between the health states. A path through the health states to the desired state of health for the patient is identified based on patient information. A set of actions for the patient is determined to traverse the health states of the path to attain the desired state of health. The machine learning model evolves based on new data to continually provide updated or new health states. This provides a dynamic arrangement that may continually change and adapt to patients. In addition, various health states may be introduced to provide more personalized sets of actions for a patient. This also reduces training or processing time as the machine learning model may be incrementally trained on new smaller training sets.

In embodiments, the health states are ranked based on one of patient preference and resilience of the patient determined from results of standardized assessment instruments. This enables the embodiments to identify optimal paths and sets of actions that incrementally improve health according to patient tolerances. Further, the ranking reduces processing since the ranking provides a limited number of paths for improving health.

In embodiments, the transition costs between the health states are determined based on a count of transitions between the health states within the patient information and/or data from the population. This enables the embodiments to weight paths according to population tolerances and provide a personalized set of actions suitable for the patient.

In embodiments, at least one transition between the health states is absent from the patient information, and a transition cost for the at least one transition between the health states is determined based on collaborative filtering of the data from the population. This enables the embodiments to accurately predict the transition costs for identification of paths and actions with improved results.

In embodiments, identifying the path through the health states comprises selecting and performing a path identification technique of one of: identifying a shortest path independent of the transition costs; identifying a path with a lowest total transition cost; identifying a path with a lowest initial transition cost; and identifying a path with lowest individual transition costs. This enables the embodiments to identify various different paths and actions to personalize the actions for a patient for enhanced results. Further, selection of different techniques reduces processing as a longest running technique is implemented less frequently.

In embodiments, the path identification technique is selected based on a preference of the patient. This enables the embodiments to customize the identification of the path and set of actions for a patient. Further, selection of different techniques reduces processing as a longest running technique is implemented less frequently.

In embodiments, the path identification technique is selected based on a resilience of the patient determined from results of standardized assessment instruments. This enables the embodiments to customize the identification of the path and set of actions to tolerances of the patient for improved results. Further, selection of different techniques reduces processing as a longest running technique is implemented less frequently.

In embodiments, a health device is controlled to facilitate performance of the set of actions. This enables the embodiments to facilitate the identified set of actions for a path for expediting the process. Further, automated control of the health device reduces configuration time to expedite processing.

According to an aspect of the invention, a computer program product facilitates actions for a patient to attain a desired state of health. The computer program product comprises one or more computer readable storage media having program instructions collectively stored on the one or more computer readable storage media. The program instructions are executable by at least one processor to cause the at least one processor to cluster, via a machine learning model, data from a population of patients to determine a plurality of health states with each cluster corresponding to a health state. Transition costs are determined for transitioning between the health states. A path through the health states to the desired state of health for the patient is identified based on patient information. A set of actions for the patient is determined to traverse the health states of the path to attain the desired state of health. The machine learning model evolves based on new data to continually provide updated or new health states. This provides a dynamic arrangement that may continually change and adapt to patients. In addition, various health states may be introduced to provide more personalized sets of actions for a patient. This also reduces training or processing time as the machine learning model may be incrementally trained on new smaller training sets.

In embodiments, the health states are ranked based on one of patient preference and resilience of the patient determined from results of standardized assessment instruments. This enables the embodiments to identify optimal paths and sets of actions that incrementally improve health according to patient tolerances. Further, the ranking reduces processing since the ranking provides a limited number of paths for improving health.

In embodiments, the transition costs between the health states are determined based on a count of transitions between the health states within the patient information and/or the data from the population. This enables the embodiments to weight paths according to population tolerances and provide a personalized set of actions suitable for the patient.

In embodiments, at least one transition between the health states is absent from the patient information, and a transition cost for the at least one transition between the health states is determined based on collaborative filtering of the data from the population. This enables the embodiments to accurately predict the transition costs for identification of paths and actions with improved results.

In embodiments, identifying the path through the health states comprises selecting and performing a path identification technique of one of: identifying a shortest path independent of the transition costs; identifying a path with a lowest total transition cost; identifying a path with a lowest initial transition cost; and identifying a path with lowest individual transition costs. This enables the embodiments to identify various different paths and actions to personalize the actions for a patient for enhanced results. Further, selection of different techniques reduces processing as a longest running technique is implemented less frequently.

In embodiments, the path identification technique is selected based on a preference of the patient. This enables the embodiments to customize the identification of the path and set of actions for a patient. Further, selection of different techniques reduces processing as a longest running technique is implemented less frequently.

In embodiments, the path identification technique is selected based on a resilience of the patient determined from results of standardized assessment instruments. This enables the embodiments to customize the identification of the path and set of actions to tolerances of the patient for improved results. Further, selection of different techniques reduces processing as a longest running technique is implemented less frequently.

In embodiments, a health device is controlled to facilitate performance of the set of actions. This enables the embodiments to facilitate the identified set of actions for a path for expediting the process. Further, automated control of the health device reduces configuration time to expedite processing.

In an example scenario, a patient is evaluated for different aspects (e.g. mood, pain, etc.) at an initial visit to a medical service provider. This may be determined based on various patient attributes (e.g., physiological attributes, mood, state of mind, etc.). An initial health state is assigned to a current condition of the patient. An optimal path is determined through health states (derived based on a population) from the initial state to a desired target state (e.g., a healthy or improved state). The path may be selected based on patient preference, or patient resilience. A next health state along the path for the patient is identified. Once the next state to achieve is identified, the aspects to be improved (or triggers) are retrieved. For example, a trigger for the patient to transition to the next state (healthier state) may be an increase in physical activity. After a better health state is achieved, the next state along the path and corresponding trigger are identified to enable transition along the path. This process is repeated until achieving the desired health state for the patient.

Various aspects of the present disclosure are described by narrative text, flowcharts, block diagrams of computer systems and/or block diagrams of the machine logic included in computer program product (CPP) embodiments. With respect to any flowcharts, depending upon the technology involved, the operations can be performed in a different order than what is shown in a given flowchart. For example, again depending upon the technology involved, two operations shown in successive flowchart blocks may be performed in reverse order, as a single integrated step, concurrently, or in a manner at least partially overlapping in time.

A computer program product embodiment ("CPP embodiment" or "CPP") is a term used in the present disclosure to describe any set of one, or more, storage media (also called "mediums") collectively included in a set of one, or more, storage devices that collectively include machine readable code corresponding to instructions and/or data for performing computer operations specified in a given CPP claim. A "storage device" is any tangible device that can retain and store instructions for use by a computer processor. Without limitation, the computer readable storage medium may be an electronic storage medium, a magnetic storage medium, an optical storage medium, an electromagnetic storage medium, a semiconductor storage medium, a mechanical storage medium, or any suitable combination of the foregoing. Some known types of storage devices that include these mediums include: diskette, hard disk, random access memory (RAM), read-only memory (ROM), erasable programmable read-only memory (EPROM or Flash memory), static random access memory (SRAM), compact disc read-only memory (CD-ROM), digital versatile disk (DVD), memory stick, floppy disk, mechanically encoded device (such as punch cards or pits/lands formed in a major surface of a disc) or any suitable combination of the foregoing. A computer readable storage medium, as that term is used in the present disclosure, is not to be construed as storage in the form of transitory signals per se, such as radio waves or other freely propagating electromagnetic waves, electromagnetic waves propagating through a waveguide, light pulses passing through a fiber optic cable, electrical signals communicated through a wire, and/or other transmission media. As will be understood by those of skill in the art, data is typically moved at some occasional points in time during normal operations of a storage device, such as during access, de-fragmentation or garbage collection, but this does not render the storage device as transitory because the data is not transitory while it is stored.

The claims and scope of the subject application, and any continuation, divisional or continuation-in-part applications claiming priority to the subject application, exclude embodiments (e.g., systems, apparatus, methodologies, computer program products and computer readable storage media) directed to implanted electrical stimulation for pain treatment and/or management.

Referring to FIG. 1, computing environment 100 contains an example of an environment for the execution of at least some of the computer code involved in performing the inventive methods, such as health analysis code 200. In addition to block 200, computing environment 100 includes, for example, computer 101, wide area network (WAN) 102, end user device (EUD) 103, remote server 104, public cloud 105, and private cloud 106. In this embodiment, computer 101 includes processor set 110 (including processing circuitry 120 and cache 121), communication fabric 111, volatile memory 112, persistent storage 113 (including operating system 122 and block 200, as identified above), peripheral device set 114 (including user interface (UI) device set 123, storage 124, and Internet of Things (IoT) sensor set 125), and network module 115. Remote server 104 includes remote database 130. Public cloud 105 includes gateway 140, cloud orchestration module 141, host physical machine set 142, virtual machine set 143, and container set 144.

COMPUTER 101 may take the form of a desktop computer, laptop computer, tablet computer, smart phone, smart watch or other wearable computer, mainframe computer, quantum computer or any other form of computer or mobile device now known or to be developed in the future that is capable of running a program, accessing a network or querying a database, such as remote database 130. As is well understood in the art of computer technology, and depending upon the technology, performance of a computer-implemented method may be distributed among multiple computers and/or between multiple locations. On the other hand, in this presentation of computing environment 100, detailed discussion is focused on a single computer, specifically computer 101, to keep the presentation as simple as possible. Computer 101 may be located in a cloud, even though it is not shown in a cloud in FIG. 1. On the other hand, computer 101 is not required to be in a cloud except to any extent as may be affirmatively indicated.

PROCESSOR SET 110 includes one, or more, computer processors of any type now known or to be developed in the future. Processing circuitry 120 may be distributed over multiple packages, for example, multiple, coordinated integrated circuit chips. Processing circuitry 120 may implement multiple processor threads and/or multiple processor cores. Cache 121 is memory that is located in the processor chip package(s) and is typically used for data or code that should be available for rapid access by the threads or cores running on processor set 110. Cache memories are typically organized into multiple levels depending upon relative proximity to the processing circuitry. Alternatively, some, or all, of the cache for the processor set may be located "off chip." In some computing environments, processor set 110 may be designed for working with qubits and performing quantum computing.

Computer readable program instructions are typically loaded onto computer 101 to cause a series of operational steps to be performed by processor set 110 of computer 101 and thereby effect a computer-implemented method, such that the instructions thus executed will instantiate the methods specified in flowcharts and/or narrative descriptions of computer-implemented methods included in this document (collectively referred to as "the inventive methods"). These computer readable program instructions are stored in various types of computer readable storage media, such as cache 121 and the other storage media discussed below. The program instructions, and associated data, are accessed by processor set 110 to control and direct performance of the inventive methods. In computing environment 100, at least some of the instructions for performing the inventive methods may be stored in block 200 in persistent storage 113.

COMMUNICATION FABRIC 111 is the signal conduction path that allows the various components of computer 101 to communicate with each other. Typically, this fabric is made of switches and electrically conductive paths, such as the switches and electrically conductive paths that make up busses, bridges, physical input/output ports and the like.

Other types of signal communication paths may be used, such as fiber optic communication paths and/or wireless communication paths.

VOLATILE MEMORY 112 is any type of volatile memory now known or to be developed in the future. Examples include dynamic type random access memory (RAM) or static type RAM. Typically, volatile memory 112 is characterized by random access, but this is not required unless affirmatively indicated. In computer 101, the volatile memory 112 is located in a single package and is internal to computer 101, but, alternatively or additionally, the volatile memory may be distributed over multiple packages and/or located externally with respect to computer 101.

PERSISTENT STORAGE 113 is any form of non-volatile storage for computers that is now known or to be developed in the future. The non-volatility of this storage means that the stored data is maintained regardless of whether power is being supplied to computer 101 and/or directly to persistent storage 113. Persistent storage 113 may be a read only memory (ROM), but typically at least a portion of the persistent storage allows writing of data, deletion of data and re-writing of data. Some familiar forms of persistent storage include magnetic disks and solid state storage devices. Operating system 122 may take several forms, such as various known proprietary operating systems or open source Portable Operating System Interface-type operating systems that employ a kernel. The code included in block 200 typically includes at least some of the computer code involved in performing the inventive methods.

PERIPHERAL DEVICE SET 114 includes the set of peripheral devices of computer 101. Data communication connections between the peripheral devices and the other components of computer 101 may be implemented in various ways, such as Bluetooth connections, Near-Field Communication (NFC) connections, connections made by cables (such as universal serial bus (USB) type cables), insertion-type connections (for example, secure digital (SD) card), connections made through local area communication networks and even connections made through wide area networks such as the internet. In various embodiments, UI device set 123 may include components such as a display screen, speaker, microphone, wearable devices (such as goggles and smart watches), keyboard, mouse, printer, touchpad, game controllers, and haptic devices. Storage 124 is external storage, such as an external hard drive, or insertable storage, such as an SD card. Storage 124 may be persistent and/or volatile. In some embodiments, storage 124 may take the form of a quantum computing storage device for storing data in the form of qubits. In embodiments where computer 101 is required to have a large amount of storage (for example, where computer 101 locally stores and manages a large database) then this storage may be provided by peripheral storage devices designed for storing very large amounts of data, such as a storage area network (SAN) that is shared by multiple, geographically distributed computers. IoT sensor set 125 is made up of sensors that can be used in Internet of Things applications. For example, one sensor may be a thermometer and another sensor may be a motion detector.

NETWORK MODULE 115 is the collection of computer software, hardware, and firmware that allows computer 101 to communicate with other computers through WAN 102. Network module 115 may include hardware, such as modems or Wi-Fi signal transceivers, software for packetizing and/or de-packetizing data for communication network transmission, and/or web browser software for communicating data over the internet. In some embodiments, network control functions and network forwarding functions of network module 115 are performed on the same physical hardware device. In other embodiments (for example, embodiments that utilize software-defined networking (SDN)), the control functions and the forwarding functions of network module 115 are performed on physically separate devices, such that the control functions manage several different network hardware devices. Computer readable program instructions for performing the inventive methods can typically be downloaded to computer 101 from an external computer or external storage device through a network adapter card or network interface included in network module 115.

WAN 102 is any wide area network (for example, the internet) capable of communicating computer data over non-local distances by any technology for communicating computer data, now known or to be developed in the future. In some embodiments, the WAN 102 may be replaced and/or supplemented by local area networks (LANs) designed to communicate data between devices located in a local area, such as a Wi-Fi network. The WAN and/or LANs typically include computer hardware such as copper transmission cables, optical transmission fibers, wireless transmission, routers, firewalls, switches, gateway computers and edge servers.

END USER DEVICE (EUD) 103 is any computer system that is used and controlled by an end user (for example, a customer of an enterprise that operates computer 101), and may take any of the forms discussed above in connection with computer 101. EUD 103 typically receives helpful and useful data from the operations of computer 101. For example, in a hypothetical case where computer 101 is designed to provide a recommendation to an end user, this recommendation would typically be communicated from network module 115 of computer 101 through WAN 102 to EUD 103. In this way, EUD 103 can display, or otherwise present, the recommendation to an end user. In some embodiments, EUD 103 may be a client device, such as thin client, heavy client, mainframe computer, desktop computer and so on.

REMOTE SERVER 104 is any computer system that serves at least some data and/or functionality to computer 101. Remote server 104 may be controlled and used by the same entity that operates computer 101. Remote server 104 represents the machine(s) that collect and store helpful and useful data for use by other computers, such as computer 101. For example, in a hypothetical case where computer 101 is designed and programmed to provide a recommendation based on historical data, then this historical data may be provided to computer 101 from remote database 130 of remote server 104.

PUBLIC CLOUD 105 is any computer system available for use by multiple entities that provides on-demand availability of computer system resources and/or other computer capabilities, especially data storage (cloud storage) and computing power, without direct active management by the user. Cloud computing typically leverages sharing of resources to achieve coherence and economies of scale. The direct and active management of the computing resources of public cloud 105 is performed by the computer hardware and/or software of cloud orchestration module 141. The computing resources provided by public cloud 105 are typically implemented by virtual computing environments that run on various computers making up the computers of host physical machine set 142, which is the universe of physical computers in and/or available to public cloud 105. The virtual computing environments (VCEs) typically take the form of virtual machines from virtual machine set 143 and/or containers from container set 144. It is understood that these VCEs may be stored as images and may be transferred among and between the various physical machine hosts, either as images or after instantiation of the VCE. Cloud orchestration module 141 manages the transfer and storage of images, deploys new instantiations of VCEs and manages active instantiations of VCE deployments. Gateway 140 is the collection of computer software, hardware, and firmware that allows public cloud 105 to communicate through WAN 102.

Some further explanation of virtualized computing environments (VCEs) will now be provided. VCEs can be stored as "images." A new active instance of the VCE can be instantiated from the image. Two familiar types of VCEs are virtual machines and containers. A container is a VCE that uses operating-system-level virtualization. This refers to an operating system feature in which the kernel allows the existence of multiple isolated user-space instances, called containers. These isolated user-space instances typically behave as real computers from the point of view of programs running in them. A computer program running on an ordinary operating system can utilize all resources of that computer, such as connected devices, files and folders, network shares, CPU power, and quantifiable hardware capabilities. However, programs running inside a container can only use the contents of the container and devices assigned to the container, a feature which is known as containerization.

PRIVATE CLOUD 106 is similar to public cloud 105, except that the computing resources are only available for use by a single enterprise. While private cloud 106 is depicted as being in communication with WAN 102, in other embodiments a private cloud may be disconnected from the internet entirely and only accessible through a local/private network. A hybrid cloud is a composition of multiple clouds of different types (for example, private, community or public cloud types), often respectively implemented by different vendors. Each of the multiple clouds remains a separate and discrete entity, but the larger hybrid cloud architecture is bound together by standardized or proprietary technology that enables orchestration, management, and/or data/application portability between the multiple constituent clouds. In this embodiment, public cloud 105 and private cloud 106 are both part of a larger hybrid cloud.

Figure 2:
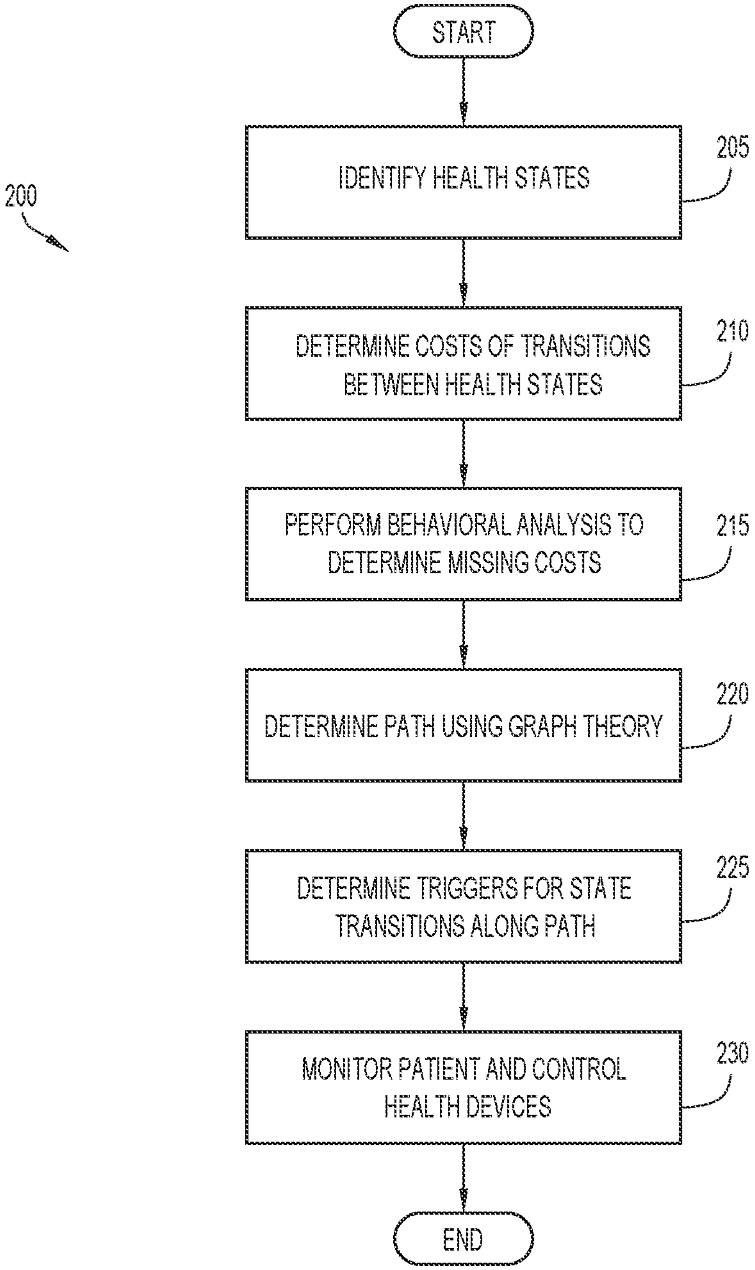
FIG. 2 is a procedural flowchart illustrating a manner of monitoring a patient and facilitating a course of action according to an embodiment of the present invention.

A method 200 of monitoring a patient and facilitating courses of action for the patient (e.g., via computer 101 and health analysis code 200, etc.) according to an embodiment of the present invention is illustrated in FIG. 2. Initially, input data may include patients with longitudinal clinical data (e.g., demographics, self-assessment (e.g., mood, etc.), etc.). The data is processed with various operations, including factorization, imputations with collaborative filtering, and graph theory. An optimal trajectory (or path) for each patient is produced with identification of triggers for performing transitions between states.

Health analysis code 200 identifies health states using several previously determined clinical attributes or features from a large cohort of patients (e.g., Number of patients (N)>100, etc.) at operation 205. The cohort preferably corresponds to a medical condition of a patient seeking to improve their state of health. The attributes or features may indicate different aspects of the patients, such as fitness level, mood, medication use, amount of sleep, etc. The health states include various attributes or characteristics (e.g., fitness level, mood, medication use, amount of sleep, state of mind, etc.), and indicate a level of health for the patient. The health states may be ranked to indicate a scale for a level of health (e.g., ranked from poorest health to healthiest, etc.). The ranking may be based on patient preference, or patient resilience or tolerance determined from standardized assessment instruments (e.g., fear avoidance and beliefs questionnaire, etc.). For example, the health states may be ranked with healthier states associated with greater resilience and less healthy states associated with lower resilience.

Health analysis code 200 determines transition costs (e.g., costs of transitions between health states, etc.) at operation 210. The transition costs may be determined based on patient preference (e.g., patient provided transition costs, etc.), or a frequency or count of transitions in data for the patient and/or in a population cohort. The transition costs may further be determined based on triggers (e.g., actions or conditions for transitioning between states, etc.). The transition costs may include a penalty associated with the characteristic (or limitation) of each patient. The transition costs may be normalized to a desired range.

Since some health states may be bypassed by the patient and/or other patients in the cohort or population, there may be transitions without an associated transition cost. Accordingly, health analysis code 200 imputes the missing transition costs based on behavioral analysis among patients at operation 215.

Once the transition costs are identified, a graph or state diagram (e.g., FIG. 3 and FIG. 6) is basically formed with nodes representing the health states and edges connecting nodes representing transitions. The edges are associated with triggers (e.g., actions, conditions, etc.) enabling traversal of the edge and a corresponding transition cost for the transition.

Health analysis code 200 determines an optimal path through the graph for the patient to transition from a current health state to an improved or optimal health state (e.g., healthy state, etc.) at operation 220. A patient may include any user, individual, subject, or other entity with or without medical service provider care or supervision. The path may be determined based on any conventional or other graph theory techniques (e.g., Dijkstra shortest path techniques, etc.). The path may be selected based on patient preference, or patient resilience (e.g., determined based on personality from results of standardized assessment instruments (e.g., fear avoidance and beliefs questionnaire, etc.), etc.). The standardized assessment instruments may include any conventional or other assessment tools, such as cognitive tests, fitness assessment tests, Oswestry Disability Index (ODI), Pain Catastrophizing Scale (PCS), Beck Depression Inventory-Second Edition (BDI-II), Fear-Avoidance Beliefs Questionnaire (FABQ), Percent Pain Relief (PPR), and/or EuroQol 5 Dimensions 5 Level (EQ5D-5L).

For example, a patient may desire to attain the optimal health state in a short amount of time and, therefore, a shortest path may be determined. Further, the path may be selected based on patient resilience, where greater resilience may produce a shorter path and less resilience may produce a longer path. By way of example, a shortest path independent of transition costs may be selected when the resilience of the patient is high, a path with the lowest total transition cost may be selected when the resilience of the patient is medium-high, a path with the lowest initial transition cost may be selected when the resilience of the patient is medium-low, and a path with the lowest individual transition costs may be selected when the resilience of the patient is low. The level of resistance may be based on a numeric value derived from the standardized assessment instruments for resilience and applied to a range for resilience levels.

Health analysis code 200 determines the triggers (or set of actions) for traversing the determined path to the improved or optimal health state at operation 225 (e.g., increase over the counter medication, physical therapy, etc.). This may be accomplished by a patient providing the triggers or actions, or comparing attributes (e.g., amount of medication, sleep, exercise, physical therapy, etc.) between health states (or clusters) to determine differences. For example, health states may differ in an amount of medication, exercise, and/or sleep, and the trigger or actions may be to adjust the amount of medication, exercise, and/or sleep at a current state to transition to, and attain, the amount of medication, exercise, and/or sleep of the next state. Thus, a path may be personalized to a patient and include states requiring adjustment to the various attributes for the patient (e.g., medication, sleep, exercise, physical therapy, etc.).

Health analysis code 200 may further monitor a patient (e.g., based on wearable sensors, data entered by the patient, etc.) and control various health devices at operation 230 to assist the patient in satisfying the triggers and transitioning along the path (e.g., control a medication dispensing device to adjust administration of medication (e.g., increase or decrease a dosage, alter frequency, etc.), control an exercise device to alter an exercise program (e.g., time duration, frequency, intensity, etc.), control a medical device to monitor patient characteristics (e.g., exercise, physiological attributes (e.g., heart rate, blood pressure, etc.), etc.), control an external electrical stimulator to provide, disable, or adjust stimulation, control an alarm system to notify a patient (e.g., for medicine, exercise, etc.), etc.).

Figure 3:
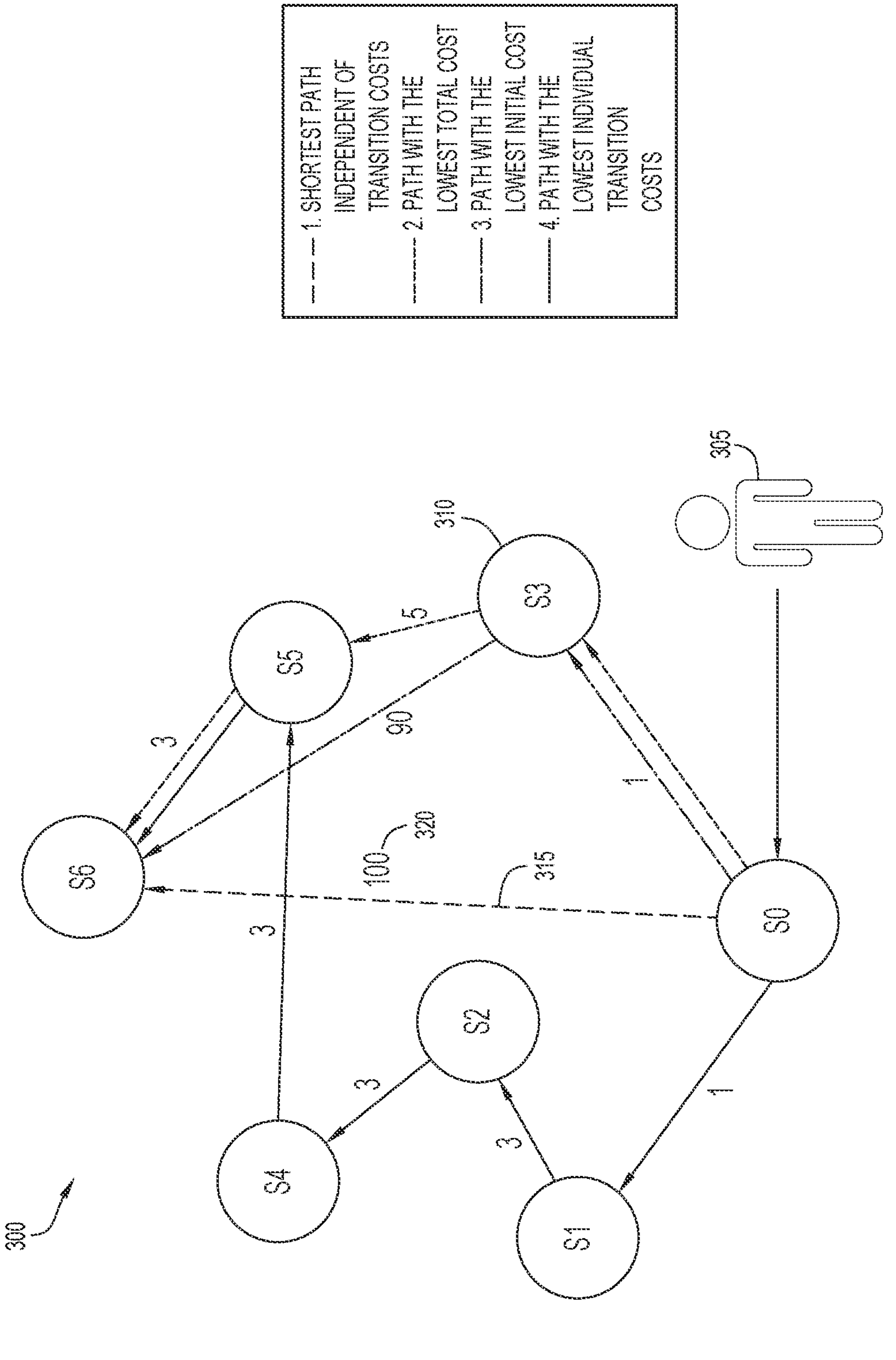
FIG. 3 is an illustration of an example state diagram providing courses of action for transitioning a patient between health states according to an embodiment of the present invention.

An example graph or state diagram 300 providing health states and courses of action for transitioning a patient between the health states according to an embodiment of the present invention is illustrated in FIG. 3. State diagram 300 includes a series of nodes 310 each associated with a corresponding health state (e.g., S0-S6 as viewed in FIG. 3). A health state indicates a state of health of a patient as described above, and may be based on various attributes (e.g., symptoms experienced, physiological readings, mood, state of mind, quality of life, etc.). The attributes may be collected from a cohort or population as described above. The health states typically progress from a lowest state of health to improved states of health (e.g., from S0-S6, with S0 indicating a low or poor state of health and S6 indicating a healthy state). The nodes are connected to other nodes by edges 315. A node 310 may be connected to one or more other nodes by corresponding edges. Each edge is associated with a transition cost 320 and a trigger for transitioning along the edge to another node. The transition cost may be determined based on patient preference (e.g., patient provided transition costs, etc.), a frequency or count of transitions in data of the patient and/or a population cohort, and/or a trigger as described above. The transition cost may represent a probability for a patient to transition to another health state. The trigger may include any actions or conditions (e.g., attaining certain physiological readings, state of mind, performing activities (e.g., medication, exercise, physical therapy, etc.), etc.).

By way of example, a transition cost of 1 may be associated with transitioning from state S0 to either state S1 or state S3, a transition cost of 3 may be associated with transitioning from state S1 to state S2, from state S2 to state S4, from state S4 to state S5, and state S5 to state S6, a transition cost of 5 may be associated with transitioning from state S3 to state S5, a transition cost of 90 may be associated with transitioning from state S3 to state S6, and a transition cost of 100 may be associated with transitioning between state S0 and state S6.

A patient 305 is initially assessed to determine a current health state for the patient (e.g., any user, individual, subject, or other entity with or without medical service provider care or supervision, etc.). This may be determined based on various patient attributes (e.g., physiological attributes, mood, state of mind, etc.). In this example case, patient 305 is initially assessed to be in state S0, and desires to attain healthy state S6. The graph or state diagram is analyzed to determine a path personalized for the patient from state S0 to state S6. The determination may be based on various objectives, such as a shortest path independent of transition costs, a path with the lowest total transition cost, a path with the lowest initial transition cost, or a path with the lowest individual transition costs. The objectives may be selected based on patient preference (e.g., provided by the patient, etc.), or a resilience of a patient (e.g., a path with the lowest individual transition costs may be determined for patients with low resilience, while a shortest path independent of transition costs may be determined for patients with high resilience, etc.).

By way of example: a shortest path independent of transition costs may include a path with a transition from state S0 to state S6; a path with the lowest total transition cost may include a path with transitions from state S0 to state S3, state S3 to state S5, and state S5 to state S6; a path with the lowest initial transition cost may include a path with transitions from state S0 to state S3, and state S3 to state S6; and a path with the lowest individual transition costs may include a path with transitions from state S0 to state S1, state S1 to state S2, state S2 to state S4, state S4 to state S5, and state S5 to state S6.

Once an appropriate path is determined (e.g., based on the objective associated with patient 305), the patient performs the actions (or other activities to satisfy the conditions) of the triggers to transition between the states in the path. This enables the patient to traverse the path to attain a healthy state (e.g., from state S0 to state S6).

Figure 4:
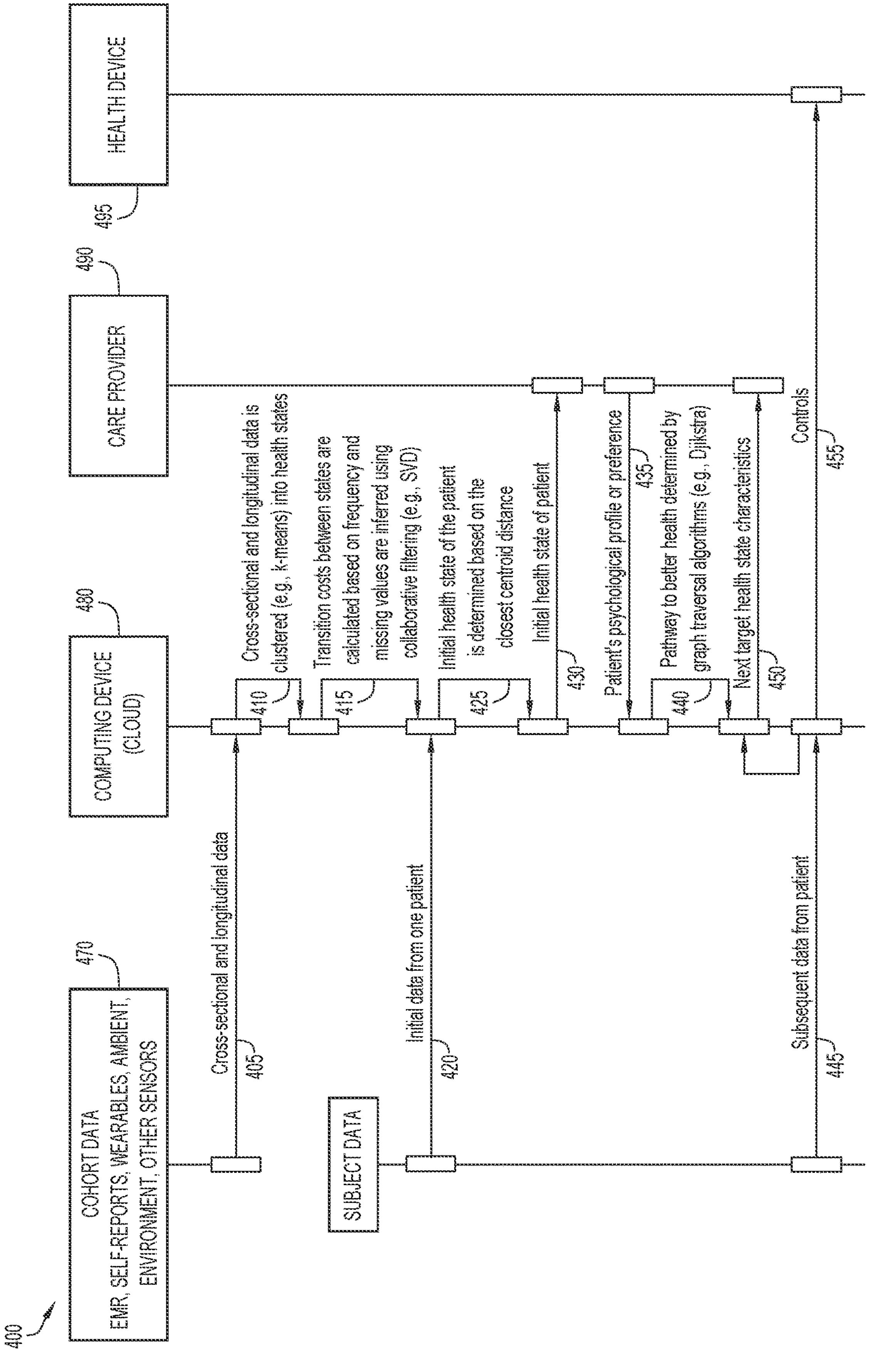
FIG. 4 is a flow diagram illustrating a manner of monitoring a patient and facilitating a course of action to transition the patient to a healthy state according to an embodiment of the present invention.

A method 400 of monitoring a patient and facilitating a course of action for the patient to transition the patient to a healthy state (e.g., via health analysis code 200 and computer 101, etc.) according to an embodiment of the present invention is illustrated in FIG. 4. Initially, various data of a patient or other population are collected (e.g., from electronic medical records (EMR), self-reports, lab work, questionnaires (e.g. to ascertain mood, depression, quality of life, resilience, etc.), wearable devices, ambient, environment, or other sensors, etc.) to form cohort data 470. The population preferably includes patients with medical conditions corresponding to a medical condition of a patient seeking to improve their state of health (e.g., similar medical condition, disease, symptoms, etc.). Cross-sectional and longitudinal data from cohort data 470 are provided to a computing device 480 at operation 405. Longitudinal data may include measurements of the same variables for a population over extended periods of time, while cross-sectional data may include data of a population captured at an instant of time. Computing device 480 may be computer 101 (or other computing device of computing environment 100), and is preferably a computing device for a cloud environment.

Computing device 480 (e.g., via health analysis code 200) clusters the cross-sectional and longitudinal data into health states at operation 410. The health states are determined using several previously determined clinical attributes or features from a large cohort of patients (e.g., Number of patients (N)>100, etc.). The features may indicate different aspects of the patients, such as fitness level, mood, medication use, etc. The clustering may employ any conventional or other clustering techniques (e.g., k-means clustering, etc.), and use any quantity of any features.

The cluster analysis identifies common features in the population, and determines results based on the presence or absence of the features in data for patients from the population. The cluster analysis may use a k-means clustering technique, however any conventional or other clustering techniques (e.g., hierarchical clustering, etc.) may be used to cluster the functions.

A machine learning model may cluster the cohort data in a feature space (of patient features) by processing the patient features. The formed clusters are each associated with a health state. For example, the clusters may each be associated with a health state, where the clustering identifies the patient features associated with the health states of the clusters. Different features (e.g., physiological attributes, demographics, mood, state of mind, etc.) may form reference points for forming the clusters.

The machine learning model may be implemented by any conventional or other machine learning models (e.g., mathematical/statistical models, classifiers, feed-forward, recurrent or other neural networks, etc.). For example, neural networks may include an input layer, one or more intermediate layers (e.g., including any hidden layers), and an output layer. Each layer includes one or more neurons, where the input layer neurons receive input (e.g., feature vectors), and may be associated with weight values. The neurons of the intermediate and output layers are connected to one or more neurons of a preceding layer, and receive as input the output of a connected neuron of the preceding layer. Each connection is associated with a weight value, and each neuron produces an output based on a weighted combination of the inputs to that neuron. The output of a neuron may further be based on a bias value for certain types of neural networks (e.g., recurrent types of neural networks).

The weight (and bias) values may be adjusted based on various training techniques. For example, a machine learning model may be trained with a training set of features, where the neural network attempts to produce the provided or known data and uses an error from the output (e.g., difference between inputs and outputs) to adjust weight (and bias) values. The output layer of the neural network indicates a cluster for input data. By way of example, the output layer neurons may indicate a specific cluster or an identifier of the specific cluster (and a probability or confidence). Further, output layer neurons may be associated with different clusters and indicate a probability (or confidence) of the input data belonging to the associated cluster. The cluster associated with the highest probability is preferably selected for the input data.

The machine learning model may be trained with data of various cohorts with known clusters or classifications. The cross sectional and longitudinal data are provided to the machine learning model to produce the clusters or health states.

The health states may be ranked to indicate a level of health (e.g., ranked from poorest health to healthiest, etc.). The ranking may be based on patient preference, or patient resilience or tolerance determined from results of standardized assessment instruments (e.g., fear avoidance and beliefs questionnaire, etc.). The standardized assessment instruments may include any conventional or other assessment tools, such as cognitive tests, fitness assessment tests, Oswestry Disability Index (ODI), Pain Catastrophizing Scale (PCS), Beck Depression Inventory-Second Edition (BDI-II), Fear-Avoidance Beliefs Questionnaire (FABQ), Percent Pain Relief (PPR), and/or EuroQol 5 Dimensions 5 Level (EQ5D-5L).

For example, the health states may be ranked with healthier states associated with greater resilience of cluster members and less healthy states associated with lower resilience of cluster members.

Once the health states are determined, computing device 480 (e.g., via health analysis code 200) determines transition costs between the health states at operation 415. The transition costs may be determined based on patient preference (e.g., patient provided transition costs, etc.), or a frequency or count of transitions in data of the patient and/or a population cohort. The transition costs may further be determined based on triggers (e.g., actions or conditions for transitioning between states, etc.). The transition costs may include a penalty associated with the characteristic (or limitation) of each patient. The transition costs may be normalized to a desired range. Since some health states may be bypassed by the patient and/or other patients in the cohort data, there may be transitions without an associated transition cost (or absent from the cohort data). Accordingly, computing device 480 (e.g., via health analysis code 200) further imputes or infers the missing transition costs based on behavioral analysis among patients at operation 415.

Figure 5:
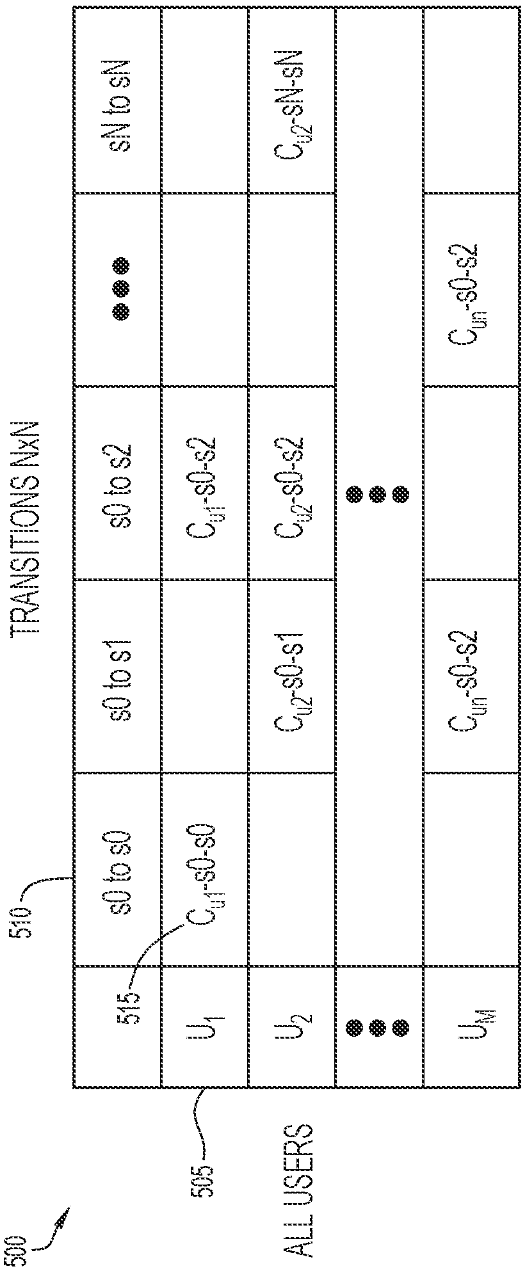
FIG. 5 is an illustration of a transition matrix according to an embodiment of the present invention.

For example, a transition matrix 500 may be generated as illustrated in FIG. 5. The transition matrix may be in the form of a table with each row 505 corresponding to a user or patient and each column 510 corresponding to a transition between a pair of health states. A row 505 for a user includes a transition cost 515 in corresponding columns for transitioning between the health states associated with the corresponding column (e.g., $C_{u1}$-s0-s0 indicates a transition cost for user 1 to transition from state S0 to state S0 (or remain in state S0), $C_{u2}$-s0-s1 indicates a transition cost for user 2 to transition from state S0 to state S1, etc. as viewed in FIG. 5). The columns encompass each possible transition between the health states. In order to determine an optimal path or trajectory for a patient, the transition matrix should include a transition cost associated with each transition. However, a training or population dataset may lack a transition cost for each transition (e.g., one or more transitions may be absent in the dataset for a patient, etc.). Accordingly, an imputation or inference technique is employed to determine missing transition costs for transitions in transition matrix 500. The inference technique may be any conventional or other prediction or inference techniques (e.g., collaborative filtering, singular value decomposition (SVD), etc.).

By way of example, a collaborative filtering technique may be employed that includes singular value decomposition (SVD). Collaborative filtering basically predicts individual user preferences from preference information of a significant number of users. SVD identifies features of users and objects, and predicts values (e.g., transition costs) based on the features. Each user or transition has a feature vector, where a prediction function (e.g., dot product of feature vectors, etc.) is used to predict transition costs based on the feature vectors. The prediction may be optimized by minimizing a sum of squared errors between existing transition costs in the transition matrix and predicted transition costs.

The collaborative filtering (or singular value decomposition (SVD)) may be used to determine the missing transition costs for a patient based on transition costs and features of other users and transitions in transition matrix 500. In other words, the collaborative filtering determines missing transition costs based on transition costs of other similar patients.

Referring back to FIG. 4, once the transition costs are identified, the transition matrix represents a graph or state diagram (e.g., FIG. 3 and FIG. 6) with nodes representing clusters or health states and edges connecting nodes representing transitions. The edges are associated with a corresponding transition cost and triggers (e.g., actions, conditions, etc.) enabling traversal of the edge.

Computing device 480 (e.g., via health analysis code 200) receives information from a patient at operation 420, and determines an initial health state of the patient at operation 425. The information form the patient may include various features or attributes (e.g., fitness level, physiological measurements, medication use, etc.). In other words, the patient is analyzed to determine a closest cluster (or health state) based on attributes of the patient and members of the cluster. For example, the features of the patient may be used to form a feature vector, while features of members of the cluster may be used to form individual feature vectors or a combined feature vector for the cluster (e.g., average or otherwise combine the features of the cluster members, etc.). The identification of a closest cluster may be accomplished by determining a closest centroid distance between the feature vector of the patient and the feature vectors of members of the clusters or of the cluster itself. However, any distance or similarity measure may be used (e.g., Euclidean distance, cosine similarity, etc.). The closest cluster is identified based on the closest feature vector (e.g., smallest distance to a feature vector of a cluster member or a feature vector for the cluster, etc.), where the health state associated with the closest cluster serves as the initial health state of the patient. The initial health state may be provided to a care provider 490 at operation 430 (e.g., displayed, sent to a user device of the care provider, etc.).

Care provider 490 may determine a psychological profile or preference of the patient, and computing device 480 receives this information at operation 435. For example, the care provider may conduct a psychological analysis, or provide a questionnaire or other standardized assessment instrument to the patient (e.g., to determine, mood, state of mind, quality of life, resilience, etc.).

Computing device 480 (e.g., via health analysis code 200) determines an optimal path through the graph for the patient to transition from the initial health state to an improved or optimal health state (e.g., healthy state, etc.) at operation 440. The path may be determined based on any conventional or other graph theory techniques (e.g., Dijkstra shortest path techniques, etc.).

In addition, the path determination may be based on the psychological profile or preference. For example, the psychological profile and patient information may be used to determine a resilience of the patient. The path determination may be based on various objectives or path identification techniques, such as a shortest path independent of transition costs, a path with the lowest total transition cost, a path with the lowest initial transition cost, or a path with the lowest individual transition costs. The objectives or path identification technique may be selected based on patient preference, or the resilience of the patient (e.g., a shortest path independent of transition costs may be selected when the resilience of the patient is high, a path with the lowest total transition cost may be selected when the resilience of the patient is medium-high, a path with the lowest initial transition cost may be selected when the resilience of the patient is medium-low, and a path with the lowest individual transition costs may be selected when the resilience of the patient is low, etc.). The level of resistance may be based on a numeric value derived from the analysis and/or standardized assessment instruments for resilience and applied to a range for resilience levels.

Computing device 480 (e.g., via health analysis code 200) receives additional information from the patient (e.g., updated and/or new features, etc.) at operation 445, and determines the triggers for traversing the determined path to a next (improved or optimal) health state at operation 445 (e.g., increase over the counter medication, physical therapy, etc.). This may be accomplished by a patient providing the triggers or actions, or comparing attributes (e.g., amount of medication, sleep, exercise, physical therapy, etc.) between health states (or clusters) and the patient to determine differences. For example, health states may differ in an amount of medication, exercise, and/or sleep, and the trigger or actions may be to adjust the amount of medication, exercise, and/or sleep of the patient at a current state to transition to, and attain, the amount of medication, exercise, and/or sleep of the next state. Thus, a path may be personalized to a patient and include states requiring adjustment to the various attributes for the patient (e.g., medication, sleep, exercise, physical therapy, etc.).

The trigger information is provided to care provider 490 at operation 450 (e.g., displayed, sent to a user device of the care provider, etc.). The care provider may assist the patient in satisfying the triggers to transition to an improved health state, In addition, computing device 480 (e.g., via health analysis code 200) may further monitor the patient and control various health devices 495 at operation 455 to assist the patient in satisfying the triggers. For example, the computing device may determine an adjustment to administration of a medication, and generate control signals to control a medication dispensing device to adjust the administration of the medication (e.g., increase or decrease a dosage, alter frequency or time of dispensing, etc.). Further, the computing device may determine an adjustment to an exercise program or activity, and generate control signals to control an exercise or activity device (e.g., treadmill, step machine, rowing machine, rehabilitation or physical therapy device, etc.) to alter an exercise or activity program (e.g., time duration, frequency, intensity, etc.). Moreover, the computing device may generate control signals to a medical device to monitor patient characteristics (e.g., exercise, physiological attributes (e.g., heart rate, blood pressure, etc.), etc.). The computing device may determine an adjustment to stimulation, and generate control signals to control an external electrical stimulator to provide, disable, or adjust stimulation. In addition, the computing device may determine an adjustment to a schedule, and generate control signals to control an alarm system to notify a patient at certain times (e.g., for medicine, exercise, etc.).

Once a next target health state is reached, the process may be repeated from the target health state to transition to a next health state in the path toward a desired health state, or determine a new path from the target state to the desired health state in substantially the same manner described above. In other words, the determined path may dynamically change at each traversed health state in response to changes in patient and/or cluster information.

An example scenario is now described with reference to FIG. 6. Initially, cohort data is collected and analyzed to produce a graph or state diagram 600. For example, the cohort data may be clustered in substantially the same manner described above, where each cluster represents a corresponding health state. The cohort preferably corresponds to a medical condition of a patient seeking to improve their state of health. Further, the health states may be ranked to indicate a level of health (e.g., ranked from poorest health to healthiest, etc.) in substantially the same manner described above.

Figure 6:
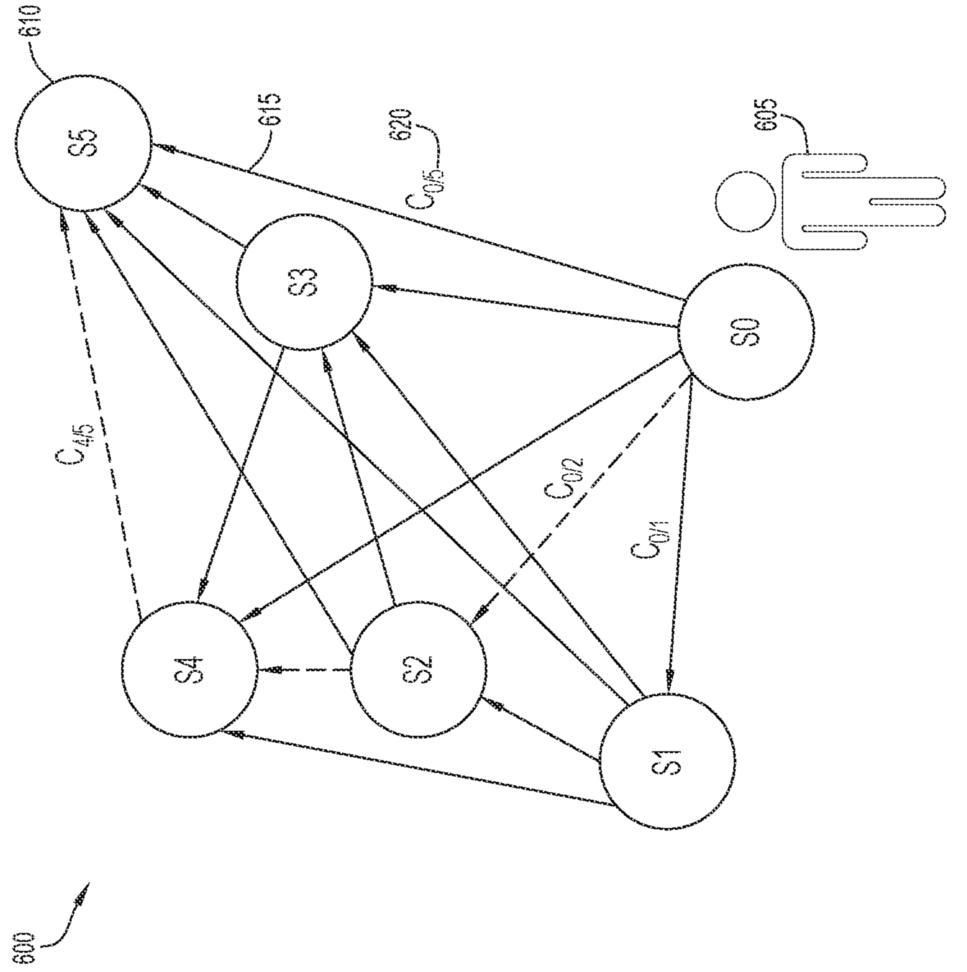
FIG. 6 is an illustration of a state diagram providing courses of action for transitioning a patient to a healthy state according to an embodiment of the present invention.

State diagram 600 includes a series of nodes 610 each associated with a corresponding health state or cluster (e.g., S0-S5 as viewed in FIG. 6). A health state indicates a level of health of a patient, and may be based on various attributes of members in the associated cluster (e.g., symptoms experienced, physiological readings, mood, state of mind, quality of life, etc.). The attributes may be collected from a cohort or population as described above. The states typically progress from a lowest state of health to improved states of health (e.g., from S0-S5, with S0 indicating a low or poor state of health and S5 indicating a healthy state).

Nodes 610 are connected to other nodes by edges 615. A node 610 may be connected to one or more other nodes by corresponding edges. Each edge is associated with a trigger and a transition cost 620 for transitioning along the edge to another node. By way of example, the transition cost is represented as $C_{initial\ state/target\ state}$ in FIG. 6 (e.g., $C_{0/5}$ represents the transition cost for transitioning from state S0 to state S5, etc.). The transition costs may be determined in substantially the same manner described above (e.g., based on patient preference, a frequency of transitions in data of the patient and/or a population cohort, triggers, etc.). The trigger may include any actions or conditions (e.g., attaining certain physiological readings, state of mind, performing activities (e.g., medication, exercise, physical therapy, etc.), etc.). The transition cost may represent a probability for a patient satisfying a trigger to transition to another health state.

A patient 605 is evaluated for different aspects (e.g. mood, pain, etc.) at an initial visit to a medical service provider. This may be determined based on various patient attributes (e.g., physiological attributes, mood, state of mind, etc.). An initial health state is assigned to a current condition of the patient in substantially the same manner described above.

An optimal path is determined through the state diagram from the initial state to a desired target state (e.g., a healthy or improved state) in substantially the same manner described above. The path may be selected based on patient preference, or patient resilience. For example, a shortest path independent of transition costs may be selected when the resilience of the patient is high, a path with the lowest total transition cost may be selected when the resilience of the patient is medium-high, a path with the lowest initial transition cost may be selected when the resilience of the patient is medium-low, and a path with the lowest individual transition costs may be selected when the resilience of the patient is low.

A next health state along the path for the patient is identified. For example, a patient was initially assigned to state S0 and the shortest path for the patient to overall improvement (state S5) is a path including states S0, S2, S4, and S5. In this example case, a next state along the path for the patient after state S0 is state S1.

Once the next state to achieve is identified, the aspects to be improved (or triggers) are retrieved. For example, a trigger for the patient to transition from state S0 to state S2 (healthier state) may be an increase in physical activity. After a better health state is achieved (e.g., state S2), the next state along the path and corresponding trigger are identified to enable transition along the path. This process is repeated until achieving the desired health state for the patient (e.g., state S5). Some patients may fail to achieve a healthiest state identified in a large population since each patient has unique characteristics. However, present invention embodiments achieve a healthiest state capable for each patient.

Present invention embodiments may provide various technical and other advantages. In an embodiment, the machine learning model may be continuously updated (or trained) based on user feedback and/or new or updated population information. For example, user feedback (e.g., preferences, etc.) and/or new or updated population information may indicate different criteria for current or new clusters. This information may be used to update or train the machine learning model with new or different training data (e.g., derived from attributes of the information, etc.) to enable dynamic determination of updated or new health states. Thus, the machine learning model may continuously evolve (or be trained) to learn characteristics of health states for dynamically changing paths or courses of action and/or improve accuracy for a patient.

It will be appreciated that the embodiments described above and illustrated in the drawings represent only a few of the many ways of implementing embodiments for monitoring and facilitating actions for a patient to attain desired health.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system. These systems may include any types of monitors and input devices (e.g., keyboard, mouse, voice recognition, etc.) to enter and/or view information.

It is to be understood that the software of the present invention embodiments (e.g., health analysis code 200, etc.) may be implemented in any desired computer language and could be developed by one of ordinary skill in the computer arts based on the functional descriptions contained in the specification and flowcharts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flowcharts may be modified in any manner that accomplishes the functions described herein. In addition, the functions in the flowcharts or description may be performed in any order that accomplishes a desired operation.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information. The database system may be implemented by any number of any conventional or other databases, data stores or storage structures (e.g., files, databases, data structures, data or other repositories, etc.) to store information. The database system may be included within or coupled to the server and/or client systems. The database systems and/or storage structures may be remote from or local to the computer or other processing systems, and may store any desired data.

The present invention embodiments may employ any number of any type of user interface (e.g., Graphical User Interface (GUI), command-line, prompt, etc.) for obtaining or providing information (e.g., sets of actions, state diagrams, etc.), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

A report may include any information arranged in any fashion, and may be configurable based on rules or other criteria to provide desired information to a user (e.g., sets of actions, etc.).

The present invention embodiments are not limited to the specific tasks or algorithms described above, but may be utilized for determining a set of actions for a user to attain any desired state (e.g., physical state (e.g., athletics, fitness, etc.), medical or health related state, mental state, etc.).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method of facilitating actions for a patient to attain a desired state of health comprising:
- clustering, via a machine learning model of at least one processor, data from a population of patients to determine a plurality of health states, wherein each cluster corresponds to a health state;
- determining, via the at least one processor, transition costs for transitioning between the health states;
- selecting, via the at least one processor and based on a preference of the patient, a path identification technique of a plurality of path identification techniques, wherein the plurality of path identification techniques comprise:
  - identifying a shortest path independent of transition costs;
  - identifying a path with a lowest total transition cost;
  - identifying a path with a lowest initial transition cost; and
  - identifying a path with lowest individual transition costs;
- identifying, via the at least one processor, a path through the health states to the desired state of health for the patient according to the path identification technique and based on patient information; and
- determining, via the at least one processor, a set of actions for the patient to traverse the health states of the path to attain the desired state of health.

2. The method of claim 1, further comprising:
- ranking the health states, via the at least one processor, based on the preference of the patient.

3. The method of claim 1, wherein determining the transition costs comprises:
- determining the transition costs between the health states based on a count of transitions between the health states within the patient information and the data from the population.

4. The method of claim 1, wherein at least one transition between the health states is absent from the patient information, and determining the transition costs comprises:
- determining a transition cost for the at least one transition between the health states based on collaborative filtering of the data from the population.

5. The method of claim 1, further comprising:
- controlling, via the at least one processor, a health device to facilitate performance of the set of actions.

6. A system for facilitating actions for a patient to attain a desired state of health comprising:
- one or more memories; and
- at least one processor coupled to the one or memories and configured to:
  - cluster, via a machine learning model, data from a population of patients to determine a plurality of health states, wherein each cluster corresponds to a health state;
  - determine transition costs for transitioning between the health states;
  - select, based on a preference of the patient, a path identification technique of a plurality of path identification techniques, wherein the plurality of path identification techniques comprise:

identifying a shortest path independent of transition costs;

identifying a path with a lowest total transition cost;

identifying a path with a lowest initial transition cost; and identifying a path with lowest individual transition costs;

identify a path through the health states to the desired state of health for the patient according to the path identification technique and based on patient information; and determine a set of actions for the patient to traverse the health states of the path to attain the desired state of health.

7. The system of claim 6, wherein the at least one processor is further configured to:

rank the health states based on the preference of the patient.

8. The system of claim 6, wherein determining the transition costs comprises:

determining the transition costs between the health states based on a count of transitions between the health states within the patient information and the data from the population.

9. The system of claim 6, wherein at least one transition between the health states is absent from the patient information, and determining the transition costs comprises:

determining a transition cost for the at least one transition between the health states based on collaborative filtering of the data from the population.

10. The system of claim 6, wherein the at least one processor is further configured to:

control a health device to facilitate performance of the set of actions.

11. A computer program product for facilitating actions for a patient to attain a desired state of health, the computer program product comprising one or more computer readable storage media having program instructions collectively stored on the one or more computer readable storage media, the program instructions executable by at least one processor to cause the at least one processor to:

cluster, via a machine learning model, data from a population of patients to determine a plurality of health states, wherein each cluster corresponds to a health state;

determine transition costs for transitioning between the health states;

select, based on a preference of the patient, a path identification technique of a plurality of path identification techniques, wherein the plurality of path identification techniques comprise:

identifying a shortest path independent of transition costs;

identifying a path with a lowest total transition cost;

identifying a path with a lowest initial transition cost; and identifying a path with lowest individual transition costs;

identify a path through the health states to the desired state of health for the patient according to the path identification technique and based on patient information; and determine a set of actions for the patient to traverse the health states of the path to attain the desired state of health.

12. The computer program product of claim 11, wherein the program instructions further cause the at least one processor to:

rank the health states based on the preference of the patient.

13. The computer program product of claim 11, wherein determining the transition costs comprises:

determining the transition costs between the health states based on a count of transitions between the health states within the patient information and the data from the population.

14. The computer program product of claim 11, wherein at least one transition between the health states is absent from the patient information, and determining the transition costs comprises:

determining a transition cost for the at least one transition between the health states based on collaborative filtering of the data from the population.

15. The computer program product of claim 11, wherein the program instructions further cause the at least one processor to:

control a health device to facilitate performance of the set of actions.

16. The method of claim 1, further comprising:

assisting the patient with respect to the set of actions, wherein the assisting comprises:

controlling a medication dispensing device to adjust administration of medication.

17. The method of claim 1, further comprising:

assisting the patient with respect to the set of actions, wherein the assisting comprises:

controlling a medical device to monitor patient characteristics.

18. The method of claim 1, further comprising:

assisting the patient with respect to the set of actions, wherein the assisting comprises:

controlling an alarm system to notify the patient.

19. The system of claim 6, wherein the at least one processor is further configured to:

assist the patient with respect to the set of actions, wherein to assist the patient with respect to the set of actions, the at least one processor is configured to:

control a medication dispensing device to adjust administration of medication.

20. The system of claim 6, wherein the at least one processor is further configured to:

assist the patient with respect to the set of actions, wherein to assist the patient with respect to the set of actions, the at least one processor is configured to:

control a medical device to monitor patient characteristics.

21. The system of claim 6, wherein the at least one processor is further configured to:

assist the patient with respect to the set of actions, wherein to assist the patient with respect to the set of actions, the at least one processor is configured to:

control an alarm system to notify the patient.

22. The computer program product of claim 11, wherein the program instructions further cause the at least one processor to:

assist the patient with respect to the set of actions, wherein to assist the patient with respect to the set of actions, the program instructions cause the at least one processor to:

control a medication dispensing device to adjust administration of medication.

23. The computer program product of claim 11, wherein the program instructions further cause the at least one processor to:

assist the patient with respect to the set of actions, wherein to assist the patient with respect to the set of actions, the program instructions cause the at least one processor to: control a medical device to monitor patient characteristics.

24. The computer program product of claim 11, wherein the program instructions further cause the at least one processor to:

assist the patient with respect to the set of actions, wherein to assist the patient with respect to the set of actions, the program instructions cause the at least one processor to: control an alarm system to notify the patient.

* * * * *